United States Patent [19]

Montemarano et al.

[11] 4,343,424
[45] Aug. 10, 1982

[54] CRACK SUSCEPTIBILITY TEST UTILIZING AN AIRPORT RESTRAINT SPECIMEN

[75] Inventors: Thomas W. Montemarano, Annapolis; Michael E. Wells, West Hyattsville, both of Md.

[73] Assignee: The United States of America as represented by the Secretary of the Navy, Washington, D.C.

[21] Appl. No.: 154,193

[22] Filed: May 29, 1980

[51] Int. Cl.³ ............................................. B21K 25/00
[52] U.S. Cl. ...................................... 228/104; 73/799
[58] Field of Search ................. 228/103, 104; 73/799, 73/850, 788

[56] References Cited

FOREIGN PATENT DOCUMENTS 620865  8/1978  U.S.S.R. .................................. 73/799

*Primary Examiner*—Mark Rosenbaum
*Assistant Examiner*—Timothy V. Eley
*Attorney, Agent, or Firm*—R. F. Beers; L. A. Marsh

[57] ABSTRACT

A crack susceptibility test for weld metals such as the alloys of titanium, aluminum and copper comprises filling a triangular pattern of grooves in a plate with weld metal wherein the groove arrangement provides the degree of restraint necessary to generate cracks in the weld metal. The grooves, which are fully contained in the plate, intersect to form a 30°-60°-90° triangle, wherein the groove depth to plate thickness ratio is between about 0.2 and 0.8.

6 Claims, 3 Drawing Figures

CRACK SUSCEPTIBILITY TEST UTILIZING AN AIRPORT RESTRAINT SPECIMEN

The invention described herein may be manufactured and used by or for the Government of the United States of America for governmental purposes without the payment of any royalties thereon or therefor.

BACKGROUND OF THE INVENTION

This invention generally relates to an improved method and apparatus for determining the weldability of metals and more particularly to a crack susceptability test especially designed for metals having a modulus of elasticity less than steel, such as titanium, aluminum and copper based alloys.

A critical factor affecting the suitability of base-filler metal combinations for various constructions is the development of cracks in the weld metal. Weldment cracking is affected by the interaction of many complex factors, such as, for example, the particular base-filler metal combination; the mechanical restraint provided by the joint structure; and the presence of low fracture toughness and high yield strength in the weld zone. Also, some materials such as titanium alloys present additional difficulties because of their high reactivity with elements such as hydrogen, oxygen, and nitrogen and because of weld embrittlement accompanying contamination by these elements.

Cracks form during the welding cycle when the strains set up by localized residual stresses and the longer range reaction stresses exceed the critical strain to initiate fracture in the weld zone. During welding, the residual strains in the weld are continuously changing as a function, for example, of localized temperatures; the overall temperature distribution in the weld zone; differential cooling and heating of the weld zone; and the sequence of metal deposition. Thus, the weld zone has a continuously changing potential for fracture and if the applied strain coincides with or exceeds the critical strain at any time or location, a crack can form.

Although the complex interaction of various factors affecting weld cracking make it difficult to predict the weldability of an alloy, several approaches have been developed to determine the suitability of a weld-filler metal combination. One approach involves the extrapolation of the results of small scale mechanical tests to predict the behavior of actual, large scale welded structures. Although the applied stresses in these tests can be accurately controlled and determined, the results often do not accurately represent the complex stress distribution in the, weld zone.

Another approach to determine the suitability of a weld-filler metal combination involves making self restrained welds under conditions which simulate the restraint achieved in actual production welds. In general, the degree of restraint can be altered by changing the dimensions and rigidity of the restraint specimen, or by using a different type of restraint specimens. Examples of crack susceptibility or crack restraint specimens are disclosed in pages 32–45 of DMIC report 244; August 1968; *Weldment Evaluation Methods*; by the Defense Metals Information Center, Battelle Memorial Institute, Columbus, Ohio.

Another example of a crack susceptibility test is disclosed in U.S. Pat. No. 3,526,948. However, crack susceptibility tests utilizing some of the tests embodied in the above-mentioned disclosures to determine the crack susceptibility of metals having a modulus of elasticity less than steel, such as titanium alloys, have failed to provide the restraint necessary to generate cracks in the weld zone.

SUMMARY OF THE INVENTION

This invention overcomes problems experienced with the prior art by providing the degree of restraint necessary to investigate the crack sensitivity and weldability of metals, especially those having a modulus of elasticity less than steel such as titanium, aluminum or copper based alloys. This is generally accomplished by forming a 30–60–90 degree triangular groove pattern in a metal alloy plate and filling the grooves with an appropriate weld metal. Generally, conventional welding processes, such as gas-metal-arc, gas-tungsten-arc, and shielded-metal-arc welding techniques, will be used wherein the weld beads are alternately deposited in the grooves and allowed to cool between each succeeding weld pass. After completion of the welding, the presence of weld cracks is determined by various means such as radiographic and/or ultrasonic tests, visual inspection, and use of penetrating dyes.

Accordingly, an object of this invention is to provide a method and means for determining the weldability of various base metal/filler metal combinations, including dissimilar combinations of copper, aluminum, nickel and iron based alloys.

Another object of the present invention is the provision of a weldability test which enables the prediction of the tendency of welds to crack without application of external stresses to the test specimen.

A further object of this invention is to provide a method and means for determining the weldability of highly restrained materials, especially those having a modulus of elasticity less than steel.

Yet another object of the present invention is to provide a weldability test which permits the generation and detection of small cracks in both the weld deposit and the heat affected zone of the test specimen.

Still another object of this invention is to provide a weldability test which permits the evaluation of different field welding procedures.

DESCRIPTION OF THE DRAWINGS

The novel features which are believed to be characteristic of this invention are set forth with particularity in the appended claims. The invention itself, however, both as to its organization and method of operation, together with further objects and advantages thereof, may be best understood by reference to the following description taken in connection with the accompanying drawings, in which:

DETAILED DESCRIPTION OF THE DRAWINGS

Figure 1:
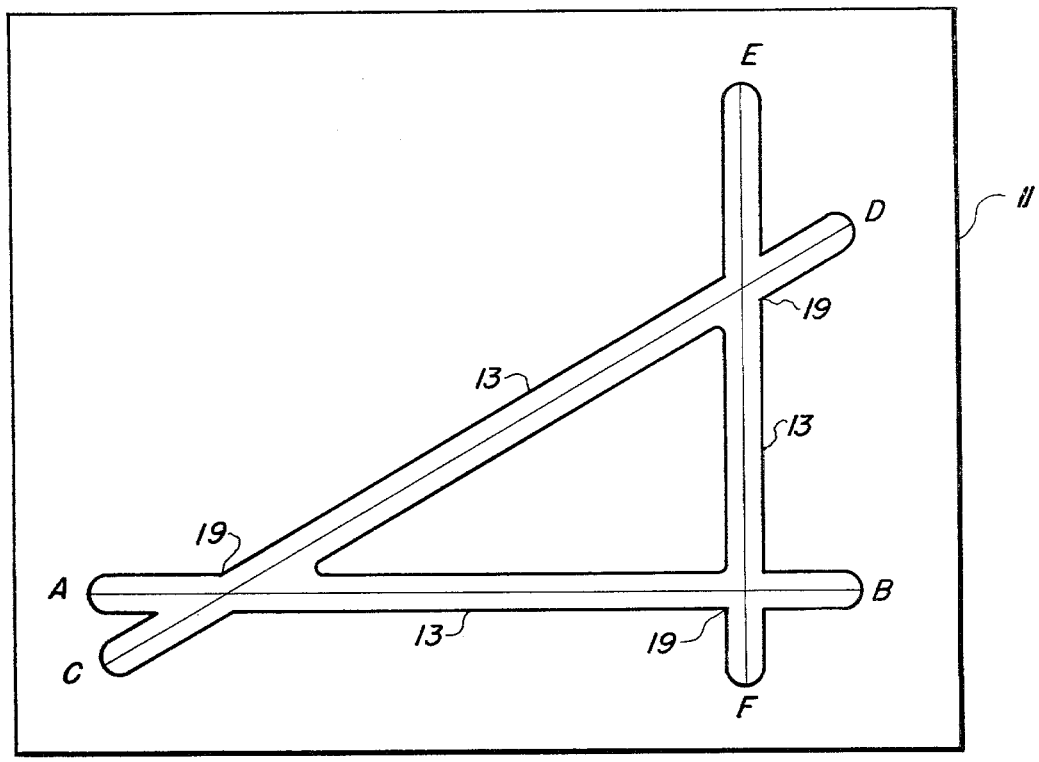
FIG. 1 is a top view of the airport restraint speciment with a triangular groove pattern formed therein.
Figure 2:
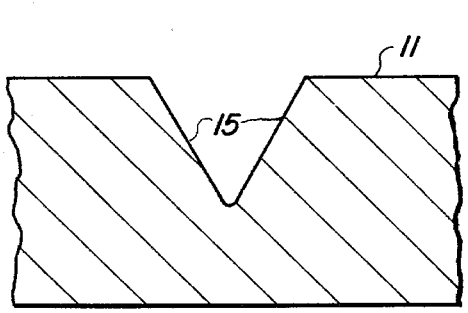
FIG. 2 is a broken away sectional view of an airport restraint specimen with a V-shaped groove formed therein.
Figure 3:
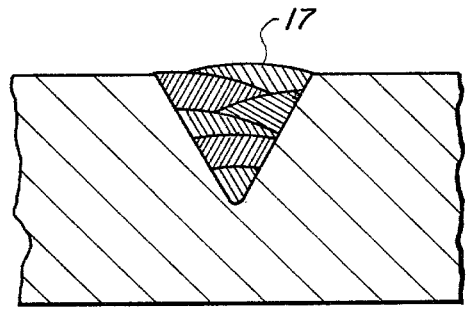
FIG. 3 is a broken away sectional view of an airport restraint specimen wherein a groove has been filled with a plurality of layers of weld beads.

Referring now to the drawings, there is generally shown in FIG. 1, a top view of the airport restraint specimen of the present invention wherein a plate 11 of the base metal is provided with a triangular arrangement of grooves 13. To simulate the weld restraint found in large scale structures, the plate 11 should have sufficient thickness to preclude distortion by the weld metal and provide the level of weld restraint necessary to exceed the critical strain to initiate cracks in the weld zone. Since more than two weld bead layers may be required to initiate cracks in the weld zones, the plate should have sufficient thickness to accomodate grooves 13 which contain a plurality of layers of weld beads 17, as shown in FIG. 3. Also, if the ratio of the groove depth to plate thickness becomes too high, the plate 11 becomes incapable of providing sufficient restraint to cause weld cracking. Thus, for example, for a plate 11 having a thickness of about two inches, the range of the ratio of groove depth to plate thickness should be between about 0.2 and about 0.8, and preferably about 0.6. Typically, the airport restraint specimen will have overall dimensions of about seventeen inches by about fifteen inches; a thickness of from about two to four inches; and grooves which range in length from about nine to about thirteen inches.

The airport restraint specimen is prepared by machining grooves 13 in the plate 11 to an appropriate depth followed by tungsten carbide burring of the groove faces 15 to a depth of about one thirty-second of an inch to remove entrapped machinery lubricants. Although the grooves 13 are preferably V-shaped with an angle of 60° formed between the faces 15 thereof, other groove shapes may be utilized which permit the desired amount of restraint to be generated in the weld zone. As shown in FIG. 1, the grooves 13, hereinafter individually designated AB, CD and EF, are arranged in a triangular pattern and fully embedded in the plate to provide the degree of restraint necessary to initiate cracking in the weld zone. Although the grooves 13, in FIG. 1, intersect to form a 30°-60°-90° triangular pattern so that the welds in the grooves 13 interact to form acute angles which thereby cause the primary stresses generated therein along the direction of welding to interact and build up, other triangular arrangements which provide the necessary weld metal restraint may also be utilized. Since the weld regions formed by the intersecting grooves 13 interact to affect the degree of restraint provided by the specimen, the dimensions of the groove arrangement may also be modified according to the particular strength characteristics of the base plate-weld metal combination.

During welding, the weld beads are normally sequentially deposited in the grooves 13 with the welds allowed to cool to an interpass temperature between each overlying weld pass. While standard field welding procedures may be used to simulate actual welding conditions, the direction of welding for a groove may be reversed between each weld pass to avoid problems such as the formation of weld craters. For example, according to such procedure the deposition sequence for two complete weld layers would be AB, CD, EF and then BA, DC, FE. Also, to prevent weld build-up at the intersecting or cross-over regions 19 of the grooves 13, the cross-over regions 19 may be reduced by selective grinding and machining. Thus, since conventional field welding techniques may be used to fill the grooves 13 and since no external forces are normally required to generate cracks in the weld zones, the cracks developed therein can be found to be a close approximation of those developed in actual structures which provide the amount of restraint which is equivalent to that provided by the airport restraint specimen.

For example, in titanium alloy test specimens, cracks which varied in length from about one-eight to about five-sixteenths of an inch were found to emanate from both pore and non-pore sites in the titanium alloy weld metal. In general, it was found that a fewer number of weld cracks occurred with welding processes which used the higher heat inputs.

Residual stress measurement of the weld deposit can be performed, for example, by the blind-hole drilling method. Briefly, rosette type strain gauges are cemented at the intersection points 19 of the grooves 13, where the most severe residual stress pattern can be expected to occur. A hole is then drilled into the weld deposit at the center of the strain gauge arrangement and the relaxation strains are measured in the vicinity of the hole. The residual stress in the weld metal is then computed from the strain measurements.

Thus the airport restraint specimen and the test method embodied thereby provides a means for evaluating weld cracking and residual stresses developed in the weld zone so that optimum welding processes and parameters can be developed. Obviously, many modifications and variations of the present invention are possible in light of the above teachings. It is therefore to be understood that within the scope of the appended claims, the invention may be practiced otherwise than as specifically described.

What is claimed is:

1. A method for testing the susceptibility of welds to cracking under conditions of heavy restraint comprises the steps of:
    forming a triangular pattern of intersecting grooves in one surface of a plate of the metal selected for welding, which plate is used to provide the restraint of the weld metal necessary to cause cracking of the weld metal;
    depositing a first layer of weld beads in the triangular pattern of grooves;
    cooling the weld layer to a predetermined temperature and inspecting the weld layer by visual and radiographic methods to detect the presence of cracks;
    depositing a predetermined number of additional layers of weld beads over the prior weld layers, allowing each to cool to a predetermined temperature and detecting the presence of cracks appearing in each successive weld layer; and
    observing the cracks which appear at selected intervals and locations in the successive weld layers and recording the resulting pattern of weld cracks.

2. A method of testing the susceptibility of weld metal to cracking comprising the steps of:
    selecting a plate of the material to be welded of a thickness to provide heavy restraint of the weld metal;
    machining a triangular pattern of intersecting grooves in the surface of the plate with the ratio of the depth of the grooves to the thickness of the plate being less than about 0.7;
    depositing a selected welding method a selected weld metal in the grooves and allowing the weld to cool; and
    inspecting the weld for cracks whereby the degree of the cracking of the weld is an indication of the compatibility of the weld metal and the metal of the plate.

3. The method of claim 2, wherein the method is applied to a succession of similar grooved plates where the method of depositing the weld metal is varied between successive plates; and comparing the degree of cracking of the welds in the successive plates to determine the optimum welding method for a particular weld metal and plate metal.

4. The method of claim 2, wherein the method is applied to a succession of similar grooved plates where the weld metal is varied from plate to plate in successive plates; and comparing the degree of cracking of the welds in the successive plates to determine the optimum weld metal and plate metal combination.

5. A method of testing the susceptibility of welds to cracking under conditions of heavy restraint comprising the steps of:

depositing layers of weld metal in a triangular pattern of intersecting grooves formed in one surface of a metal plate of material which has sufficient thickness to provide restraint of the deposited weld metal;

allowing the deposited weld metal to cool; and inspecting the deposited weld metal to determine the degree of cracking of the weld metal to indicate the weld compatiability of the weld metal and the metal of the plate.

6. A method of testing the susceptibility of welds to cracking under conditions of heavy restraint comprising the steps of:

depositing a predetermined number of layers of weld metal in a 30–60–90 degrees triangular pattern of intersecting grooves formed in one surface of a metal plate of material having sufficient thickness to provide heavy restraint of the deposited layers of weld metal;

allowing the deposited weld metal in each layer to cool to a predetermined temperature before depositing another layer of weld metal in the grooves;

observing the cracks which appear at selected intervals and locations in the layers of deposited weld metal and recording the resulting pattern of weld cracks.

* * * * *